United States Patent [19]

Flock

[11] 4,351,966

[45] Sep. 28, 1982

[54] PHENOL RECOVERY FROM BISPHENOL-A WASTE STREAMS

[75] Inventor: John W. Flock, Schenectady, N.Y.

[73] Assignee: General Electric Company, Schenectady, N.Y.

[21] Appl. No.: 271,340

[22] Filed: Jun. 8, 1971

[51] Int. Cl.³ .................. C07C 37/68; C07C 39/04
[52] U.S. Cl. .................................. 568/753; 568/806
[58] Field of Search ............ 568/753, 806, 727, 724; 252/455 Z

[56] References Cited

U.S. PATENT DOCUMENTS 3,702,886  11/1972  Argans et al. ............... 252/455 Z
3,948,760   4/1976  Gring ......................... 252/455 Z
4,036,739   7/1977  Ward .......................... 252/455 Z
4,131,749  12/1978  Kiedik et al. ................... 568/781
4,191,843   3/1980  Kwantes et al. ................. 568/724
4,277,628   7/1981  Carnahan ....................... 568/753

Primary Examiner—Werren B. Lone
Attorney, Agent, or Firm—Joseph T. Cohen; James C. Davis, Jr.

[57] ABSTRACT

Bisphenol-A waste stream derived from the reaction of phenol and acetone in the presence of an acidic condensing agent can be treated with a molecular sieve to obtain good yields of phenol present in the effluent stream either in isolated form or as part of the compounds present in the waste stream.

5 Claims, No Drawings

PHENOL RECOVERY FROM BISPHENOL-A WASTE STREAMS

This invention is concerned with a process for obtaining phenol from the residue derived during the manufacture of bisphenol-A [2,2-bis(4-hydroxyphenyl)propane], hereinafter also identified as "BPA". More particularly, the invention is directed to a method for recovering phenol from the residual tar (or waste stream) resulting from the reaction of phenol and acetone in the presence of an acidic condensation catalyst from which most of the bisphenol-A has previously been removed by treating the said tar with an effective amount of a molecular sieve (or zeolite) catalyst, and thereafter isolating the phenol thereby present in said waste stream or liberated by such treatment.

Bisphenol-A is commercially prepared by reacting phenol and acetone in the presence of an acidic material such as sulfuric acid, hydrochloric acid, cation exchange resins, etc. As a result of carrying out this reaction, the bisphenol-A produced is accompanied by the formation of undesirable impurities such as the 2-(4-hydroxyphenyl)-2-(2-hydroxyphenyl) propane (hereinafter identified as "o,p-isomer") having the formula:

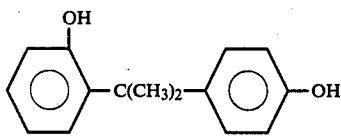

I.

as well as other impurities, including the reactant phenol itself used in making the bisphenol-A, a trishydroxyphenyl compound of the formula

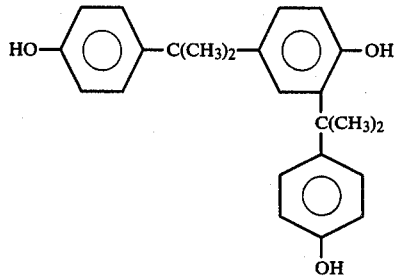

II.

small amounts of other impurities such as the two compounds having the formulas

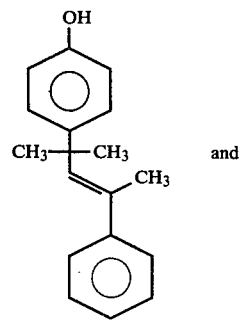

III.

and

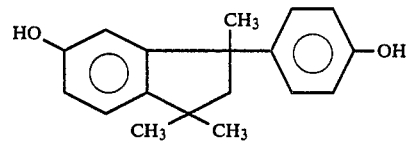

Chroman I of the formula

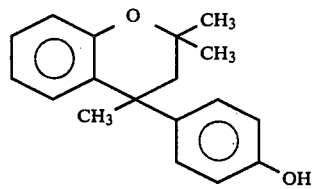

IV.

and Chroman II of the formula

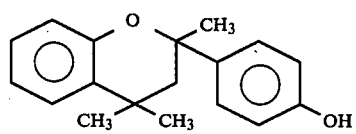

V.

The bisphenol-A produced by the above method has in the main been effectively removed from the tarry residue by a number of procedures, including distillation, crystallization, solvent extraction, spray drying, etc. There still remains the need to efficiently treat the tars and residues resulting from the initial reaction of the phenol and acetone and recover all useful products possible in order to enhance the bisphenol-A process. Included in the tars derived from the bisphenol-A reaction are certain amounts of bisphenol-A itself which is trapped therein, as well as the aforementioned free phenol. If a method could be obtained for economically and efficiently treating the residue of the bisphenol-A reaction (hereinafter referred to as "residue"), it has been calculated that millions of pounds of phenol could be recovered derived from compounds present in the residue which when cracked will provide phenol, particularly from the compounds II to VI mentioned above.

Heretofore no simple process to my knowledge has been found for cracking the tars or treating the tars in such a manner as to make it worthwhile to expend the extra effort and energy to recover phenol from the residue. As a result, the usual solution to disposal of the residue involves treating the residue as a source of energy by burning it. Unexpectedly, I have discovered that I can treat the residue with relatively small amounts of a molecular sieve catalyst at relatively modest temperatures and at atmospheric pressure, for instance, at temperatures ranging from about 200° to 500° C. whereby treated residue can then be distilled to remove substantially all of the trapped phenol and the phenol liberated from compounds in which the phenol ion was part of a compound present in the tarry residue.

The use of molecular sieve catalysts for the above purpose has several advantages. In the first place, the molecular sieve is readily available on the open market and is relatively inexpensive. Moreover, in contrast to other processes for cracking the tars which require exceptionally high temperatures and are therefore nonselective and energy intensive, the use of the molecular sieve, particularly a molecular sieve in the form of a heterogeneous catalyst, has the inherent advantage that it does not migrate from the cracking process to any other chemical processes associated with bisphenol-A, or resin manufacture based on bisphenol-A, such as polycarbonate resin manufacture, and thereby cause impurity problems.

The term "molecular sieve catalyst" (or "zeolite catalyst") as used herein and in the claims is intended to denote a crystalline hydrated silica-alumina catalyst made up predominantly (major proportion) of $SiO_2$ and a minor proportion of aluminum oxide ($Al_2O_3$), preferably in a pelletized state. The presence of very small amounts of element impurities (or cations) such as magnesium, rare earths (such as cerium), generally is not deleterious to the ability of the silica-alumina catalyst to exercise its prescribed function. The usual silica-alumina catalyst which has been found to be effective in the cracking of the tar consists generally of the 13Y form which contains $SiO_2$ and $Al_2O_3$, for example, 13Y zeolite has the formula:

$$Na_{56}[(AlO_2)_{56}(SiO_2)_{136}] \cdot 250 H_2O \qquad \text{VI.}$$

The cations are quite mobile and can be exchanged to varying degrees by other cations.

Examples of molecular sieves which can be employed in the practice of the present invention are more particularly described in a book entitled "Zeolite Molecular Sieves"—Structure, Chemistry, and Use, by Donald W. Breck, published by John Wiley & Sons (1974), New York, N.Y.; U.S. Pat. No. 3,948,760 issued Apr. 6, 1976; U.S. Pat. No. 4,033,858, issued July 5, 1977; U.S. Pat. No. 3,702,886 issued Nov. 14, 1972 and particularly the molecular sieves or zeolite catalysts described in U.S. Pat. No. 4,036,739, issued July 19, 1977, all of which describe in greater detail the type of molecular sieves (or zeolite) catalysts which can be used in the instant invention. Some of these references also describe means whereby the sodium zeolite is exchanged with ammonium ions (and heated to drive off the ammonia) to yield the decationized form of the zeolite catalyst, which are effective in the practice of the present invention. By reference, the aforementioned publication and patents are intended to be included in the disclosures and teachings of the instant application for purposes of describing the particular catalyst used for obtaining phenol from the aforesaid residue.

The above-described cation exchange resin catalysts mentioned above and in the references are important since different cations give different degrees of acidity, and the acidity of the catalyst has a great deal to do with the effectiveness of the cracking of the bisphenol-A tar. By conducting this partial or complete replacement of, for instance, the sodium cation with the other cations, (e.g., magnesium, cerium, ammonium, etc.), not only is high phenol recovery possible but in some cases by-product formation is significantly repressed.

The amount of molecular sieve catalysts which can be employed can be varied widely and generally the tarry residue is not sensitive to the amount of molecular sieve catalyst used. Advantageously, when conducting batch operations, I can employ on a weight basis from about 1 to 25%, by weight, and preferably from about 5 to 20%, by weight, of the molecular sieve catalyst, based on the weight of the residue. Generally, the residue is not so different that any significant change in the concentration of the molecular sieve catalyst will cause any undesirable variation in the amount of phenol which may be obtained or liberated. Alternatively, the residue can be passed through a heated bed of the molecular sieve catalyst.

The temperature at which the reaction is carried out can be varied widely but is usually that which is high enough to effect the desired liberation of the derived phenol without unduly causing decomposition of the desirable products. The fact that some bisphenol-A is present also will result in the latter releasing phenol as a result of practicing the invention. Generally, temperatures on the order of about 200° to 500° C. or even higher (but below the decomposition point of any of the desirable products resulting from the residue) can be employed without departing from the scope of the invention. The temperature used will depend on the rate of reaction desired, the concentration of phenol and other by-products in the residue on which the molecular sieve catalyst is intended to act, the amount of molecular sieve catalyst used, etc. Although the reaction is more conveniently carried out at atmospheric pressure, superatmospheric and subatmospheric pressures are not precluded.

In order that those skilled in the art may better understand how the present invention may be practiced, the following examples are given by way of illustration and not by way of limitation. All parts are by weight unless otherwise indicated.

The molecular sieve catalysts used in the following tests were prepared by repeatedly (about 4–6 times) ion exchanging a commercial 13Y molecular sieve (formula VI) manufactured by the Linde Division of Union Carbide Company which comes in the sodium form, i.e., sodium cations are present. The catalysts were prepared by treating, respectively, the molecular sieve with 10 percent, by weight, aqueous solutions of the chlorides of magnesium, cerium, and ammonium, at a temperature of about 90° C. until essentially all the sodium ion had been exchanged. The exchanged molecular sieves were then dried in a vacuum oven at about 180° C. for approximately 72 hours and used as such with the exception of the ammonia form, which was heated at 500° C. for about 5 hours to drive off ammonia after the exchange reaction with ammonium chloride had taken place.

The residue or tar used was obtained from the reaction of phenol and acetone to make bisphenol-A using HCl as a condensation catalyst. The residue used in the following example contained about 32% residual bisphenol-A with varying amounts of the o,p-isomer and other impurities of formulas II to VI together with a variety of related phenol-based structures. The o,p-isomer was one having the formula I and a separate residue high in its content of this isomer was also subjected to the catalyst treatment described below.

EXAMPLE 1

The tests conducted in this example consisted of charging a known amount of the bisphenol-A tar or the orthopara isomer of formula I residue, or mixtures of both residues to a 500 ml reaction vessel fitted with an electrically heated reflux column. The temperature of the column was controlled so as to allow the released phenol product to escape overhead (to a condenser and collection vessel) and to return the heavy residual material back to the reaction vessel. The reaction vessel was first heated until the reaction material therein melted and the cation exchanged zeolite catalyst was then added to the melt. Typically, about 15 grams of catalyst and 150 grams of organic (tar or isomer residues) were used in each test. The overhead product (the phenol) was collected in 10 ml lots and analyzed for phenol content by liquid chromatographic techniques. As phenol was produced and removed overhead, the composition of the tar or isomer residue remaining behind tended to become heavier in consistency and the reflux temperatures (or reaction temperature) in the reaction vessel were allowed to rise, the maximum temperature rise being limited to about 360° C. Since the condenser, through which the phenol product passed through, was open to the atmosphere, the reactions were run at essentially atmospheric pressure and at temperatures within the range of about 250° C. to 360° C. It will of course be apparent that by proper control of conditions, superatmospheric and subatmospheric pressures could be employed without departing from the scope of the invention.

The following Table I shows the results of conducting various tests under a variety of conditions, using in some instances the tar obtained from bisphenol-A production or the o,p-isomer residue, or the mixture of the tar and isomer residues, as well as the molecular sieve either decationized or exchanged with other ions to substantially remove the sodium ion present in the original molecular sieve. Tests were also conducted on the residues under the same conditions in the absence of the catalysts.

TABLE I

| | SUMMARY | | |
|---|---|---|---|
| Test No. | Residue Charges | Molecular Sieve Catalyst | [a]% Phenol |
| 1 | Tar | [b]decationized sieve | 53.12 |
| 2 | Tar | $Ce^{+3}$ exchanged | 47.89 |
| 3 | Isomer | [b]decationized sieve | 53.65 |
| 4 | [c]Tar and Isomer | [b]decationized sieve | 54.34 |
| 5 | Tar | None | 37.32 |
| 6 | Tar | $Mg^{+2}$ exchanged | 45.42 |

TABLE I-continued

| | SUMMARY | | |
|---|---|---|---|
| Test No. | Residue Charges | Molecular Sieve Catalyst | [a]% Phenol |
| 7 | Tar | [b]decationized sieve | 52.85 |
| 8 | Isomer | None | 37.10 |
| 9 | Isomer | [b]decationized sieve | 47.85 |
| 10 | [c]Isomer and Tar | [b]decationized sieve | 48.23 |
| 11 | [c]Isomer and Tar | [b]decationized sieve | 50.87 |
| 12 | [c]Isomer and Tar | $Ce^{+3}$ exchanged | 53.60 |

[a]Based on weight of residue or mixture of residues.
[b]Ammonium exchanged and thermally treated.
[c]Equal weight mixture.

It will of course be apparent to those skilled in the art that in addition to the conditions, proportions of ingredients, types of molecular sieve catalysts, and catalyst concentration used above, other conditions, proportions of ingredients, and types and concentrations of molecular sieve catalyst may be employed within the scope of the claimed invention.

What I claim as new and desire to secure by Letters Patent of the United States is:

1. The process of cracking a residue derived from the reaction of phenol and acetone in the presence of an acidic catalyst to make bisphenol-A which process comprises contacting the said residue with a molecular sieve catalyst at a temperature from 200° C. to below 500° C. to cause the liberation of phenol from the residue, and collecting the distilled phenol.

2. The process as in claim 1 wherein the amount of molecular sieve catalyst ranges from about 1 to 25%, by weight, based on the weight of the residue.

3. The process as in claim 1 wherein the molecular sieve catalyst is the 13Y silica-aluminum oxide zeolite.

4. The process as in claim 4 wherein the residue is 2-(4-hydroxyphenyl)-2-(2-hydroxyphenyl) propane residue.

5. The process as in claim 1 wherein the molecular sieve catalyst is the 13Y silica-aluminum oxide zeolite in which the sodium cation has been exchanged with magnesium or rare earth, or ammonium cations.

* * * * *

UNITED STATES PATENT AND TRADEMARK OFFICE
CERTIFICATE OF CORRECTION

PATENT NO. : 4,351,966
DATED : SEPTEMBER 28, 1982
INVENTOR(S) : John W. Flock

It is certified that error appears in the above-identified patent and that said Letters Patent are hereby corrected as shown below:

On the title page;

In the heading, the filing date reading June 8, 1971 should read June 8, 1981.

Signed and Sealed this

Twentieth Day of August 1985

[SEAL]

Attest:

DONALD J. QUIGG

Attesting Officer  Acting Commissioner of Patents and Trademarks